United States Patent [19]
Patton et al.

[11] Patent Number: 5,237,109
[45] Date of Patent: Aug. 17, 1993

[54] ETHERIFICATION PROCESS

[75] Inventors: Gary R. Patton, Bartlesville, Okla.; Curtis W. Arnold, Houston, Tex.

[73] Assignee: Phillips Petroleum Company, Bartlesville, Okla.

[21] Appl. No.: 899,407

[22] Filed: Jun. 16, 1992

Related U.S. Application Data

[63] Continuation-in-part of Ser. No. 774,504, Oct. 10, 1991, abandoned.

[51] Int. Cl.$^5$ ............................................. C07C 41/06
[52] U.S. Cl. ..................................... 568/697; 568/699
[58] Field of Search .............................. 568/647, 699

[56] References Cited

U.S. PATENT DOCUMENTS 3,979,461  9/1976  Ancillotti et al. ................... 568/697
5,091,590  2/1992  Harandi et al. ..................... 568/697

FOREIGN PATENT DOCUMENTS 0075838  4/1983  European Pat. Off. .

Primary Examiner—Howard T. Mars
Attorney, Agent, or Firm—Charles W. Stewart

[57] ABSTRACT

An etherification process for reacting tertiary olefin compounds with primary alcohols to produce an ether product. The etherification process has the advantage of permitting dual operating modes for producing methyl tertiary butyl ether and tert amyl methyl ether and it provides high conversion across the etherification process of the tertiary olefin compounds.

28 Claims, 2 Drawing Sheets

ETHERIFICATION PROCESS

This application is a continuation-in-part of application Ser. No. 07/774,504, filed Oct. 10, 1991 now abandoned.

This invention relates to the production of alkyl tertiary alkyl ether compounds.

It is known that alkyl tertiary alkyl ether compounds can be prepared by reacting primary or secondary alcohols with olefin compounds having a double bond on a tertiary carbon atom in the presence of an acidic ionic exchange resin catalyst. The particularly more common etherification reactions are those that involve reacting methanol with either isobutylene or isoamylenes to form respectively methyl tertiary butyl ether (MTBE) and methyl tertiary amyl ether (TAME). These tertiary alkyl ether compounds are particularly useful as octane improvers for liquid fuels, especially gasoline. Also, because of the low vapor pressure of these compounds, they are particularly useful for reducing the vapor pressure of gasoline. Recent federal government regulations have resulted in the requirement that motor gasoline be reformulated to include greater concentration levels of oxygenate compounds of which tertiary alkyl ether compounds have been found to be especially suitable for assisting in compliance with these new federal regulations.

While processes for the production of high octane tertiary alkyl ethers have been known in the art, there still remains various problems with the known processes that have heretofore not been resolved by those skilled in the art. In particular, because standard etherification reactions are equilibrium type reactions, most etherification processes do not provide economical means for obtaining high olefin reaction conversions without incurring high energy and capital costs to obtain such high olefin conversions. An additional problem with known etherification processes is their inability to alternatively produce either an MTBE product or a TAME product in processes that give high tertiary olefin conversions without incurring significant modifications in the process flow schemes and process equipment. Another problem encountered by those skilled in the art of etherification processing is the difficulty of removing the cyclopentene compounds, which can be contained in etherification process feeds, along with the ether product produced in the etherification reaction section of the process. It is desirable to remove any cyclopentene charge to the etherification process system concurrently with the ether product because of its potential negative effect on downstream processes to which the nonreactive compounds contained in the etherification process feedstream are fed. Finally, as is generally the case for most process technologies, it is desirable to have an etherification process that provides for high purity product streams produced at low operating costs.

It is therefore an object of this invention to provide an etherification process that produces tertiary alkyl ethers at high olefin conversion rates and low operating capital costs.

It is another object of this invention to provide an etherification process that can be operated in dual production modes for producing either MTBE or TAME, or both, and still maintain a high tertiary olefin conversion across the process.

Yet another object of this invention is to provide an etherification process that allows for the removal of a significant amount of the cyclopentene compounds contained in the feed to such process concurrently with the final tert alkyl ether product.

A still further object of this invention is to provide product streams having high purities but at low operating costs.

The process of this invention includes passing an etherification reactor effluent as a first feed to first separation means for separating feeds into a first stream comprising a first ether product and a second stream comprising primary alcohols and tertiary olefins. The second stream is passed to a reaction zone containing therein an acidic ion exchange resin and wherein the primary alcohols and tertiary olefins of said second stream react to form a second ether product contained in a reactor effluent stream. At least a portion of the reactor effluent stream is passed to first separation means while the remaining portion of the reactor effluent that is not passed to the first separation means is passed to second separation means. The remaining portion of the reactor effluent stream is passed to second separation means for separating said reactor effluent stream into a third stream comprising said second ether product and a fourth stream comprising hydrocarbons and primary alcohols.

Other objects, aspects and features of the present invention will be evident from the following detailed description of the invention, the claims and the drawings in which:

Figure 1:
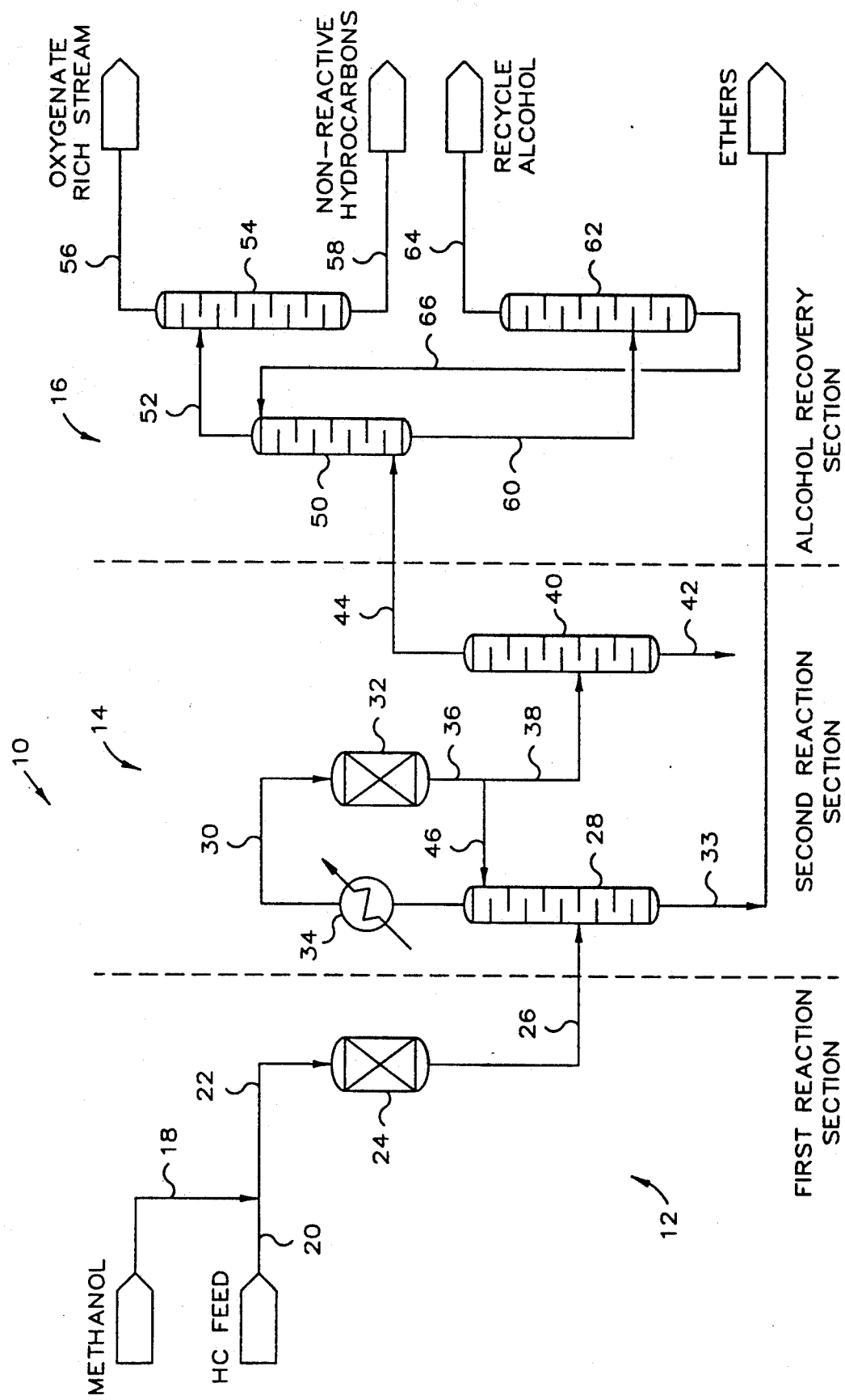
FIG. 1 is a schematic process flow diagram illustrating one preferred embodiment of the invention having three sections which include a first reaction section, a second reaction section, and an alcohol recovery section.

The inventive process has various unique features of which none of the prior art etherification processes have. For instance, one novel feature of this process is the inclusion of a second etherification reaction zone inside the reflux loop of a fractionator utilized to separate an etherification reaction product. Because the second etherification reaction zone is contained within the fractionator reflux loop, generally, and preferably, at least a portion of the etherification reaction product of the second etherification reaction zone will be passed back to the fractionator preferably as a feed and, most preferably, as a reflux. The significance of utilizing a second reaction zone in such a manner is that it provides for an exceedingly high overall conversion of reactive olefin compounds across the etherification process but at significantly lower operating and capital costs than those of the prior art processes. None of the prior art discloses the utilization of a second reaction zone within the reflux loop of a fractionator overhead system for the purpose of providing high tertiary olefin conversion and low energy and capital costs.

The inventive process includes two separate reaction sections and an alcohol recovery section. Each of the reaction sections has a reactor vessel used to define a reaction zone containing therein a suitable etherification catalyst for promoting or catalyzing an etherification reaction between reactive tertiary olefin compounds and primary or secondary alcohols. A feedstream comprising tertiary olefins and primary alcohols is charged or fed to the first reaction zone of the first reaction section of the process wherein it is contacted with the etherification catalyst under suitable reaction conditions for promoting the reaction of the tertiary olefins and alcohols contained in the feedstream to produce an etherification reactor effluent or a first reaction section effluent stream.

The first reaction section effluent stream is then passed to a second reaction section wherein it is first separated by separation means for separating the stream into a first ether product stream containing the etherification reaction products and another stream containing the nonreactive compounds, isoolefins and alcohols charged to the first reaction section of the process but which remained unconverted. The stream containing the nonreactive compounds, and unreacted isoolefins and alcohols is then contacted with an acidic ion exchange resin catalyst, which is the same or substantially similar to the catalyst used in the first reaction section and which is contained in a reactor vessel defining a reaction zone, under suitable etherification reaction conditions, to produce a second reaction section reactor effluent stream. This second reaction section reactor effluent stream is then divided into two streams with an optional portion of the second reaction section reactor effluent stream going to second separation means for separating the ether product produced in the second reaction section from the other nonreactive compounds and unreacted isoolefins and alcohols. At least a portion of the second reaction section reactor effluent stream is fed to first separation means whereby the ether product contained therein is separated from the nonreactive compounds, isoolefins and alcohols. The preferred embodiment of the invention includes passing at least a portion of the second reaction section reactor effluent stream to the first separation means preferably as a feed and, most preferably, as a reflux. In this preferred embodiment of the invention, the remaining portion of the second reaction section reactor effluent stream not charged to first separation means is passed, or utilized as a feed, to the second separation means.

The nonreactive compounds, unreacted isoolefins and alcohols separated by second separation means are passed to an alcohol recovery section whereby the alcohols are separated and recovered for reuse from the nonreactive compounds charged to etherification process system 10 and whereby the undesirable reaction by-products produced in the two etherification reaction zones are recovered. The undesirable reaction by-products are generally oxygenate compounds; and, in particular, the most prevalent undesirable reaction by-product is dimethylether, which is a reaction product produced by reacting two molecules of methanol. The dimethylether compound is undesirable in that it has a high vapor pressure that has a negative impact on the gasoline pool by raising its overall vapor pressure. Therefore, it is desirable to remove the dimethylether compounds from the gasoline pool and utilize it elsewhere, for instance, in the fuel gas stream of a process plant. An additional problem the reaction by-product dimethylether poses is its impact on downstream alkylation processes. In the instances where dimethylethers are fed to HF alkylation processes, to which the nonreactive olefin compounds that pass through the etherification process are charged, acid consumption in such processes is dramatically increased due to the unwanted reactions with the dimethylethers in the feed. The inventive process described herein provides an effective means for removing dimethylethers from alkylation feedstreams and thus eliminating problems associated with having such compounds contained within feeds to HF alkylation processes.

The nonreactive compounds separated by the alcohol recovery section can be passed downstream for further processing; and, in the case where these compounds are predominantly hydrocarbons and, in particular, olefin hydrocarbons, they are often charged to alkylation processes wherein they are reacted with isoparaffins to produce high octane alkylate compounds. It is important that the nonreactive compound stream contain minimum concentration levels of cyclopentene due to the negative impact that such a compound has on alkylation processes. As will be further discussed herein, certain of the alternative inventive embodiments of this invention provide for minimizing the concentration levels of cyclopentene in the rejected nonreactive compounds that are passed downstream to alkylation processes. Also, various other embodiments of the inventive process provide for a high removal and recovery of the undesirable reaction by-products produced in the etherification process, namely, dimethylether.

The alcohol recovery section can be any suitable process section for separating solute components contained in solution, which in the present process is preferably a primary alcohol, from the remaining compounds of the solution, which are primarily hydrocarbons. Generally, it is preferred for the alcohol recovery section to be of the type involving conventional liquid-liquid extraction or solvent extraction methods wherein a feed solution is intimately contacted, by use of contacting means, with a solvent to produce an extract stream containing the solvent rich in the alcohol solute and a raffinate stream. The raffinate stream is lean in alcohol content and is essentially that feedstream charged to contacting means but having a substantial reduction in its alcohol content. The extract stream is passed to separation means, which is preferably a conventional fractionator, that separates the alcohol from the solvent. The separated alcohol can be recycled and utilized as a reactant feed to the first reaction section of the etherification process. The recovered solvent is recycled and reused in contacting means for recovering alcohol from its feedstream. The raffinate stream is passed to separation means for separating the raffinate into an oxygenate rich stream and a hydrocarbon stream. Conventional fractionation techniques can be used to separate the hydrocarbons from the oxygenate compounds contained in the raffinate stream. Any solvent having suitable properties for removing an alcohol solute from a hydrocarbon and alcohol solution can be utilized in the inventive process; however, the preferred solvent is water.

The feed to the first reaction section of the etherification process, as earlier described, is a mixed stream comprising a stream of primary or secondary alcohols and a stream having isoolefins and other compounds that are nonreactive in the presence of an acidic ion exchange resin catalyst at certain etherification reaction conditions. Generally, the isoolefins include those hydrocarbons having 4 to 16 carbon atoms per molecule. Examples of such isoolefins include isobutylene, isoamylene, isohexylene, isoheptylene, isooctylene, isononylene, isodecylene, isoundecylene, isododecylene, isotridecylene, isotetradecylene, isopentadecylene, and isohexadecylene, or mixtures of two or more thereof.

The alcohols which may be charged or fed to the first etherification reaction zone include the primary and secondary aliphatic alcohols having from 1 to 12 carbon atoms, such as methanol, ethanol, propanol, isopropanol, the primary and secondary butanols, pentanols, hexanols, ethylene glycol, propylene glycol, butylene glycol, the polyglycols, and glycerol, etc., or mixtures of two or more thereof.

The presently preferred reactants of the etherification process are methanol and isobutylene and/or an amylene because they respectively yield methyl tertiary butyl ether (MTBE) and methyl tertiary amyl ether (TAME). Accordingly, it is currently preferred for the isoolefins to be either predominantly isobutylene or predominantly isoamylene compounds with the double bond on the tertiary carbon atom of said isoamylene compounds, or both isobutylene and isoamylene, and the alcohol predominantly methanol.

It is generally preferred for the isoolefin and the alcohol to be passed through the etherification reaction zones in the presence of diluents which do not have an adverse effect upon the etherification reaction and which are nonreactive under the conditions of etherification. Examples of suitable diluents include alkanes and straight chain olefins. The feed to the reactors, excluding alcohol, is generally diluted so as to include from about 2 to about 80 weight percent isoolefin, preferably from about 10 to about 60 weight percent.

Any suitable molar ratio of alcohol to isoolefin in the feedstream to the etherification reactor zones can be utilized in this invention that will give the desired high tertiary olefin conversion sought to be achieved by the process of this invention. Generally, the molar ratio of alcohol to isoolefin in the feeds to the etherification reaction zones will be in the range of from about 0.5:1 to about 4:1; but, preferably, the molar ratio can range from about 0.8:1 to about 1.2:1. However, to achieve the highest conversion of the isoolefins in the process feeds to the etherification reaction zones, it is most preferable to have a molar ratio of alcohol to the isoolefin as close to 1:1 as is practically achievable.

Typical etherification reactions are well known in the art and are not a critical aspect of this invention except in the case of the second reaction zone where the operating pressure has an impact on the energy utilization of first separation means. As will be demonstrated by the examples herein, there is a positive benefit, undisclosed by the art, from operating the second etherification reaction zone at lower operating pressures in that it reduces the energy required to provide the separation performed by first separation means. The temperature for the etherification reaction zone and the space velocity for the feeds to the etherification reaction zone can be selected as desired depending upon the degree of olefin conversion sought; but, generally, they should be such to provide the highest degree of olefin conversion that is economically feasible. Generally, the temperature of the reaction zones will range upwardly to about 150° C. Preferably, the etherification reaction temperatures can range from about 30° C. to about 120° C., and most preferably, the temperature shall range from about 35° C. to about 80° C. The operating pressure of the etherification reaction zones are generally selected to ensure that the feedstreams or charges to the reaction zones and the product streams from the reaction zones remain in the liquid phase during the etherification reaction. Typical pressures are in the range of from about 30 psig to about 300 psig, but as earlier noted, it has been determined that if it is feasible to operate the second etherification reaction zone at operating pressures below 20 psig, significant reductions in the energy consumption in operating first separation means can be achieved thus making the novel process described herein much more economical to operate than the prior art processes. However, in most circumstances, the etherification reactions should be conducted in the liquid phase. Generally, the liquid hourly space velocity (LHSV) of feed to the etherification reactors will be in the range of from about 1 hour$^{-1}$ to about 20 hours$^{-1}$; but, preferably, the LHSV can be in the range of from about 2 hours$^{-1}$ to about 10 hours$^{-1}$. Most preferably, the LHSV can be in the range of from 3 hours$^{-1}$ to 5 hours$^{-1}$.

The etherification reaction is that which selectively reacts tertiary olefins with alcohol, which is preferably methanol, to form a tertiary ether compound. The etherification reaction is an equilibrium type reaction that can be represented as follows:

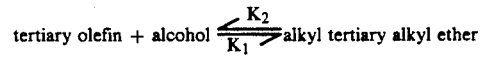

tertiary olefin + alcohol $\underset{K_1}{\overset{K_2}{\rightleftharpoons}}$ alkyl tertiary alkyl ether Due to the values and temperature dependencies of the equilibrium constants of the aforementioned reaction, the equilibrium condition which favors the formation of the tertiary ether product is a low reactor temperature condition; but, in any event, because the etherification reaction is an equilibrium type reaction, the percent conversion of the tertiary olefin contained in a reaction zone to an ether product is thermodynamically limited. It has been surprisingly found that it is possible to increase tertiary olefin conversion by carrying out the etherification reaction process in two reaction stages with the second reaction stage following a separation step, which necessarily follows a first reaction stage, and with the second reaction stage being placed within the reflux loop of a fractionator that serves as the separation step. Accordingly, the entire overhead stream from the separation step following the first reaction stage will pass to the second reaction stage with at least a portion of the resultant second reaction stage effluent passing to such separation step as a reflux.

By utilizing the novel etherification process features and improvements, high tertiary olefin conversions can be achieved. For instance, in the case of an MTBE production mode process, the isobutylene conversion across the process can exceed about 96 weight percent. Preferably, however, the isobutylene conversion exceeds about 98 weight percent, and most preferably, the isobutylene conversion can exceed 99 weight percent. As for the case of the TAME production mode process, the isoamylene conversion is not as high as that of isobutylene conversion due to the different reaction kinetics and thermodynamic relationships. However, exceedingly high isoamylene conversions are obtainable by use of the inventive process with conversions exceeding about 88 weight percent; but preferably, exceeding about 90 weight percent. The most preferred isoamylene conversion achievable from use of the novel and inventive process described herein is 92 weight percent.

The acid ion exchange catalysts utilized in the etherification reaction zones of the present invention are relatively high molecular weight carbonaceous material containing at least one SO₃H functional group. These catalysts are exemplified by the sulfonated coals ("Zeo-Karb H", "Nalcite X" and "Nalcite AX") produced by the treatment of bituminous coals with sulfuric acid and commercially marketed as zeolitic water softeners or base exchangers. These materials are usually available in a neutralized form and in this case must be activated to the hydrogen form by treatment with a strong mineral acid such as hydrochloric acid and water washed to remove sodium and chloride ions prior to use. The sulfonated resin type catalysts are preferred for use in the present invention. These catalysts include the reaction products of phenolformaldehyde resins with sulfuric acid ("Amberlite IR-1", "Amberlite IR-100" and "Nalcite MX"). Also useful are the sulfonated resinous polymers of coumarone-indene with cyclopentadiene, sulfonated polymers of coumarone-indene with cyclopentadiene, and furfural and sulfonated polymers of cyclopentadiene with furfural. The most preferred cationic exchange resins are strongly acidic exchange resins consisting essentially of sulfonated polystyrene resin. These resins are manufactured and sold commercially under various trade names such as "Dowex 50", "Nalcite HCR" and "Amberlyst 15". As commercially obtained, they have solvent contents of about 50 percent and can be used as is or the solvent can be removed first. The resin particle size is not particularly critical and therefore is chosen in accordance with the manipulative advantages associated with any particular size. Generally mesh sizes of 10 to 50 U.S. Sieve Series are preferred. The reaction may be carried out in either a stirred slurry reactor or in a fixed bed continuous flow reactor. The catalyst concentration in a stirred slurry reactor should be sufficient to provide the desired catalytic effect. Generally catalyst concentration should be 0.5 to 50 percent (dry basis) by weight of the reactor contents with from 1 to 25 percent being the preferred range.

Acid ion exchange resins, such as Rohm & Haas Amberlyst 15 and Dow Chemical Dowex M-31, are currently the most preferred catalysts for the etherification.

Now referring to FIG. 1, there is provided a schematic representation of etherification process system 10 having a first reaction section 12, a second reaction section 14, and an alcohol recovery section 16.

An alcohol feedstream, which preferably contains methanol, is charged to etherification process system 10 via conduit 18. A hydrocarbon feedstream, containing the reactive isoolefins of either isobutylene or isoamylene, or both, and a nonreactive diluent, is charged via conduit 20 to etherification process system 10. The two streams passing through conduits 18 and 20 are mixed together prior to passing by way of conduit 22 to first etherification reactor vessel 24, which defines a first etherification reaction zone wherein is contained an acidic ion exchange resin catalyst as described herein. The first etherification reaction zone is operated under suitable etherification reaction conditions so as to react at least a portion of the tertiary olefins with the alcohols contained in the feedstream to first etherification reactor vessel 24 to produce a first etherification reactor effluent.

The first etherification reactor effluent passes via conduit 26 to first separation means 28 for separation of its feeds into a first stream comprising the ether product produced from the reactions that take place in first etherification reactor vessel 24 and a second stream containing unreacted alcohols, unreacted tertiary olefins and at least a substantial amount of the compounds contained in the incoming hydrocarbon feedstream that are nonreactive under the etherification reaction conditions at which first etherification reactor vessel 24 operates. First separation means 28 can be any equipment or process which suitably can separate ether compounds from a stream comprising primary alcohols and hydrocarbon compounds, but it is preferred that first separation means 28 be a typical conventional distillation column that defines a separation zone and which can comprise a rectifying zone and a stripping zone. In the novel process described herein, first separation means 28, or in the preferred case, first distillation column or first fractionator 28, will separate the first etherification reactor effluent into an overhead stream containing primary alcohols and hydrocarbons that passes as an overhead stream via conduit 30 to second etherification reactor vessel 32 and a bottoms stream containing a first ether product that is conveyed from fractionator 28 via conduit 33.

Second etherification reactor vessel 32 defines a second etherification reaction zone wherein is contained an acidic ion exchange resin catalyst identical to the type utilized in the first etherification reaction zone. Interposed in conduit 30 is heat exchanger 34 defining a heat transfer zone utilized for removing heat energy from the overhead stream leaving first separation means 28. The second etherification reactor effluent stream leaves second etherification reactor vessel 32 via conduit 36. At least a portion of the second etherification reactor effluent stream passes by way of conduit 46 to first separation means 28. A remaining portion of the second etherification reactor effluent stream, after at least a portion of the second etherification reactor effluent stream is passed to first separation means 28, preferably as a feed, and most preferably as a reflux, is passed by way of conduit 38 to second separation means 40. Second separation means 40 can be any suitable means for separating the remaining portion of said second etherification reactor effluent stream into a third stream comprising the ether product produced by the reaction of tertiary olefins with primary alcohols in second etherification reactor vessel 32 and another stream comprising hydrocarbons, primary alcohols and any by-products produced in the previous two etherification reaction zones. It is preferable, however, that second separation means 40 be a conventional distillation column or fractionator which defines a separation zone. In the use of the preferred distillation equipment, the bottoms product from second separation means 40 will comprise ether compounds produced in second etherification reactor vessel 32 and passes from second separation means 40 by way of conduit 42. The overhead stream from second separation means 40 will comprise unreacted hydrocarbons, primary alcohols and undesirable reaction by-products that pass by way of conduit 44 to alcohol recovery section 16 whereby the alcohol compounds are separated from the unreacted hydrocarbons and other undesirable reaction by-products such as dimethylether.

The remaining portion of the second etherification reactor effluent not fed or charged to first separation means 28 is fed to second separation means 40 by way of conduit 38. In the case where first separation means 28 is in the form of a conventional distillation column, the at least a portion of the second reactor product can be fed at any location along the column, but it is preferable to utilize the at least a portion of the second etherification reactor effluent as a reflux stream. It has been found that an essential feature of this invention is that the second etherification reactor vessel 32 should be interposed within the reflux loop of first fractionator 28, with at least a portion of the second etherification reactor effluent passing to first fractionator 28, for this invention to provide the benefits of high tertiary olefin conversion rates and low energy consumption. Therefore, while this invention is broad enough to encompass the use of at least a portion of the second etherification reactor effluent as a feed anywhere along a distillation column that is utilized as first separation means 28, it is highly preferable for the at least a portion of the second etherification reactor effluent to be utilized as a reflux to first fractionator 28.

The overhead stream from second separation means 40 passes to contacting means 50 for contacting an extraction solvent or solvent with the overhead stream charged to contacting means 50 by way of conduit 44. Contacting means 50 can be any suitable piece of equipment for contacting a solvent with a feed solution containing a solute, which in the instant case is alcohol, and preferably, contacting means 50 will be a contacting vessel defining a contacting zone and can be equipped with either trays or packing for assisting in the intimate contacting of the solution and solvent. Contacting means 50 produces a raffinate stream, which is substantially free of alcohol, and an extract stream comprising a solvent rich in alcohols. The raffinate stream is removed as an overhead stream from contacting means 50 and passes by way of conduit 52 to third separating means 54 for separating the raffinate stream into a stream comprising oxygenates, which are primarily dimethylethers, and a stream comprising hydrocarbons. Third separating means 54 can be any equipment suitable for separating a raffinate stream comprising oxygenate compounds and hydrocarbon compounds; but, preferably, third separating means 54 is a distillation column or fractionator that defines a separation zone. The overhead stream from third separating means 54 passes downstream by way of conduit 56 and the bottoms stream from third separating means 54 passes downstream by way of conduit 58. The extract stream from contacting means 50 is a solvent utilized for recovering the primary alcohols from the feedstream charged to contacting means 50 which is rich in primary alcohols. The extract stream, comprising the solvent rich in primary alcohols, passes by way of conduit 60 to fourth separating means 62 for separating the extract solvent rich in primary alcohols into an alcohol stream and a stream of recovered solvent lean in primary alcohols. Fourth separating means 62 can be any equipment suitable for separating the primary alcohols from the solvent that is charged to it and will preferably be a conventional distillation column or fractionator defining a separation zone. The overhead from fourth separating means 62 is the separated alcohol and passes by way of conduit 64 from fourth separating means 62. The recovered solvent, which is lean in primary alcohols, is recycled back to contacting means 50 by way of conduit 66 and is utilized as the solvent for contacting means 50.

Figure 2:
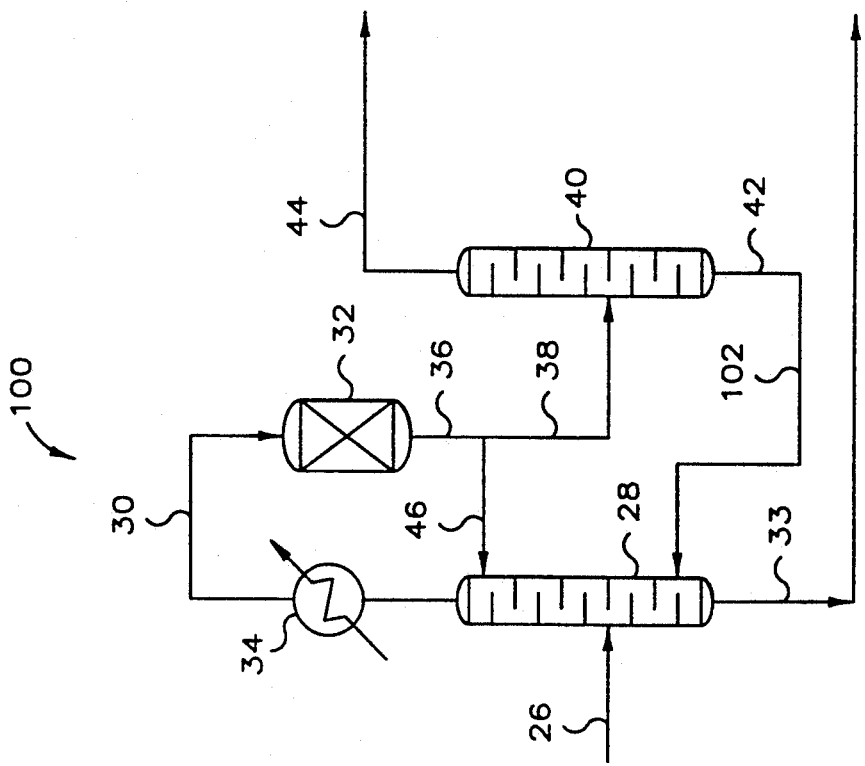
FIG. 2 is a schematic process flow diagram illustrating an alternative embodiment of the second reaction section of the inventive process.

Another embodiment of the invention is depicted in FIG. 2, which shows second reaction section 100 having a somewhat different flow scheme from that illustrated in FIG. 1 for second reaction section 14. The feature distinguishing second reaction section 100 from second reaction section 14 is that the bottom stream from second separation means 40, instead of passing downstream to either storage or further processing, is recycled via conduit 102 to first separation means 28 as a feed to the separation zone defined by separation means 28 and preferably as a feed to the stripping zone of separation means 28. Utilizing this bottom stream as a feed to first separation means 28 provides various significant advantages over other alternative flow schemes in that it assists in removing a substantial portion of the cyclopentene from etherification process system 10 that enters it by way of the hydrocarbon feed charged to first reaction section 12. This is a desirable advantage in that by removing the cyclopentene at this stage of the process, it is prevented from passing with the raffinate stream of alcohol recovery section 16. Cyclopentene is an undesirable compound for downstream alkylation processes; and, if it is not removed prior to being passed with the raffinate stream, it ends up in the hydrocarbon stream that passes by way of conduit 58 to downstream processing. An additional advantage of the embodiment depicted in FIG. 2 is that the bottoms stream from second separation means 40 can be passed as a hot stream to first separation means 28 and can be utilized to provide additional reboil heat that may be required for fractionation. In other words when distillation methods are utilized for first separation means 28 and second separation means 40, the utilization of the bottom stream from second separation means 40 as a feed to first separation means 28 provides for heat integration of the two distillation columns thereby lowering overall energy costs associated with the production of ether compounds by novel etherification process system 10.

Figure 3:
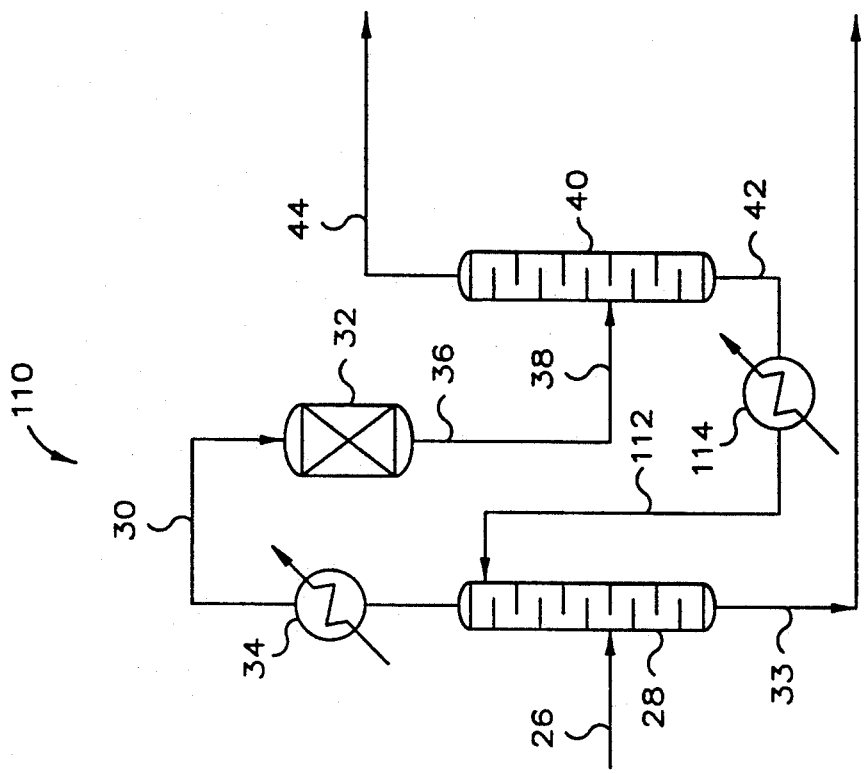
FIG. 3 is a schematic process flow diagram illustrating another embodiment of the second reaction section of the inventive process.

Another embodiment of the invention is illustrated in FIG. 3 where a third type of second etherification reaction section 110 is depicted. Second reaction section 110 is similar to second reaction section 14 with several significant differences. The first difference between the second reaction sections is that essentially all the reactor effluent leaving second etherification reactor vessel 32 passes to second separation means 40 with none of the reactor effluent passing to first separation means 28. Additionally, the bottoms product from second separation means 40 passes by way of conduits 42 and 112 to first separation means 28 and is utilized as reflux in the case where first separation means 28 is a conventional fractionator. Interposed in conduit 112 is heat exchanger 114 used to cool the bottom stream from second separation means 40 prior to feeding said stream to first separation means 28 as a reflux. Heat exchanger 114 defines a heat transfer zone for the indirect transfer of heat energy from the bottom stream to a cooling medium.

The following examples are presented in further illustration of the invention.

EXAMPLE I

The following calculated example is to illustrate the benefits achievable from the novel process as illustrated in FIG. 1 when compared with a similar process, but one which does not have the improvements incorporated in the invention of this process, disclosed in U.S. Pat. No. 3,979,461. The comparative process is different from the process of this invention in that it does not have a second reaction zone contained in the reflux loop of the first distillation tower of a two reactor stage etherification process. Table I shows the feedstream composition to the TAME etherification process and Table II provides pertinent process information for the two processes including such information as the tertiary olefin conversion across the process and energy requirements for the separation towers of each process. Also provided in Tables III and IV are data for the processes in the MTBE production mode. Table III shows the feedstream composition utilized for the inventive and comparative processes in the MTBE production mode. Table IV provides pertinent process information which includes tertiary olefin conversion and process energy requirements for the inventive process and for the comparative process.

TABLE I

TAME Production Mode Feed Composition

| Feed | Wt. % |
|---|---|
| 2-Methyl-1-Butene | 6.12 |
| 2-Methyl-2-Butene | 32.08 |
| Isopentane | 18.07 |
| 1-Pentene | 2.80 |
| cis-2-Pentene | 36.03 |
| Isoprene | 4.90 |
| | 100.00 |

TABLE II

Calculated Results for TAME Process

| | Inventive Process | Comparison Process |
|---|---|---|
| Isoamylene Conversion (wt. %) | 92.45 | 82.51 |
| TAME Product Purity (vol. % TAME) | 96.67 | 94.99 |
| Raffinate (wppm TAME) | <1 | <1 |
| (wppm heavy alcohol) | 5 | 3 |
| Column #1 | | |
| Reboiler (MM BTU/Hr) | 31.59 | 23.94 |
| Condenser (MM BTU/Hr) | 35.51 | 24.22 |
| Reboiler (°F.) | 262 | 264 |
| Condenser (°F.) | 159 | 146 |
| Reboiler (psia) | 50 | 55 |
| Condenser (psia) | 45 | 45 |
| Diameter (Ft.) | 9 | 7.5 |
| Theoretical trays | 15 | 30 |
| Column #2 | | |
| Reboiler (MM BTU/Hr) | 7.41 | 8.78 |
| Condenser (MM BTU/Hr) | 8.41 | 10.41 |
| Reboiler (°F.) | 221 | 237 |
| Condenser (°F.) | 110 | 110 |
| Reboiler (psia) | 35 | 35 |
| Condenser (psia) | 20 | 20 |
| Diameter (Ft.) | 4.5 | 5 |
| Theoretical trays | 30 | 30 |

TABLE III

MTBE Production Mode Feed Composition

| Feed | Wt. % |
|---|---|
| propane | 10.27 |
| normal butane | 10.02 |
| isobutane | 25.59 |
| isobutylene | 13.91 |
| cis-2-butene | 23.33 |
| 1-butene | 11.54 |
| isopentane | 5.34 |
| | 100.00 |

TABLE IV

Calculated Results for MTBE Process

| | Inventive Process | Comparison Process |
|---|---|---|
| $IC_4^=$ Conversion (wt. %) | 99.23 | 99.48 |
| MTBE Product Purity (vol. % MTBE $C_5$ free) | 96.82 | 87.51 |
| Raffinate (wppm MTBE) | 9 | 5 |

TABLE IV-continued

Calculated Results for MTBE Process

| | Inventive Process | Comparison Process |
|---|---|---|
| (wppm heavy alcohol) | <1 | <1 |
| Column #1 | | |
| Reboiler (MM BTU/Hr) | 7.43 | 8.29 |
| Condenser (MM BTU/Hr) | 8.34 | 8.43 |
| Reboiler (°F.) | 281 | 281 |
| Condenser (°F.) | 161 | 142 |
| Reboiler (psia) | 145 | 155 |
| Condenser (psia) | 140 | 140 |
| Diameter (Ft.) | 4 | 4.5 |
| Theoretical trays | 15 | 30 |
| Column #2 | | |
| Reboiler (MM BTU/Hr) | 8.48 | 8.14 |
| Condenser (MM BTU/Hr) | 8.57 | 8.31 |
| Reboiler (°F.) | 217 | 181 |
| Condenser (°F.) | 110 | 110 |
| Reboiler (psia) | 100 | 100 |
| Condenser (psia) | 85 | 85 |
| Diameter (Ft.) | 4 | 4 |
| Theoretical trays | 30 | 30 |

As can be seen from the data presented in Table II, a significant improvement in the isoamylene conversion is achievable by the inventive process with the isoamylene conversion improving from 82.5 wt. percent to 92.5 wt. percent. This almost 10 wt. percent improvement in isoamylene conversion is an unexpected result from utilizing a second etherification reactor within the reflux loop of a distillation tower of an etherification process and provide as a relux to the distillation tower at least a portion of the second etherification reactor effluent. Generally, those skilled in the art would expect that there would be no significant difference between placing an etherification reactor in the reflux loop of the first fractionator of the process as opposed to placing the reactor outside the reflux loop of such process. The data presented for the MTBE production mode case demonstrate that the inventive process can be utilized in an MTBE production mode as well as a TAME production mode without any significant negative impact upon the process, yields and tertiary olefin conversions. Due to the ability of the inventive process to operate in both a TAME production mode and MTBE production mode, one of the objectives of the inventive process is additionally achieved.

EXAMPLE II

This calculated example illustrates some of the benefits that are achievable from alternative embodiments of the inventive process. Table V provides calculated process data for the inventive process in the TAME production mode for both a base or primary embodiment of the invention and a second embodiment of the invention as depicted in FIG. 2. The calculated data presented in Table V is based on a feed composition similar, but not identical, to that expressed in Table I above with the primary differences in the compositions being in the non-reactive components.

TABLE V

Calculated Process Data for TAME Production Mode and Alternative Embodiment

| | Primary Embodiment | Alternative Embodiment |
|---|---|---|
| TAME Yield Based on TAME Balance | 91.89 | 92.08 |
| Steam Requirement | | |
| 40 psig (M #/Hr) | 44.2 | 62.23 |

TABLE V-continued
Calculated Process Data for TAME Production Mode and Alternative Embodiment

|  | Primary Embodiment | Alternative Embodiment |
|---|---|---|
| 150 psig (M #/Hr) | 0 | 0 |
| TAME Product | | |
| Purity (Vol. %) | 90.4 | 88.9 |
| RVP | 4 | 4 |
| C$_5$ Product | | |
| vppm TAME | 10 | 0 |
| vppm tertiary amyl alcohol | 22 | 0 |
| Vol. % cyclopentene | 3.67 | 1.04 |
| Mol. % cyclopentene | 4.36 | 1.25 |
| Column 1 BTM RVP | 3 | 4 |
| Column 2 BTM RVP | 8.5 | 12 |
| Heating Duties (MM BTU/Hr) | | |
| Column 1 Preheater | 0 | 0 |
| Column 1 Reboiler | 32.65 | 34.44 |
| Reactor 2 Preheater | 3.76* | 4.00* |
| Column 2 Preheater | 0 | 0 |
| Column 2 Reboiler | 7.94 | 22.75 |
| Temperatures (°F.) | | |
| Column 1 Bottom | 228 | 214 |
| Column 1 Condenser | 106 | 107 |
| Column 2 Bottom | 173 | 153 |
| Column 2 Condenser | 106 | 104 |
| Pressures (psia) | | |
| Column 1 Bottom | 30 | 30 |
| Column 1 Condenser | 20 | 20 |
| Column 2 Bottom | 30 | 30 |
| Column 2 Condenser | 20 | 20 |
| Estimated Sizes | | |
| Column 1 Diameter (Ft.) | 9.5 | 9.5 |
| Column 2 Diameter (Ft.) | 4.5 | 8.0 |

*Duty supplied via heat exchange with process streams.

The data presented in Table V illustrates that there are some benefits from using the alternative process, as earlier mentioned, of reducing the amount of cyclopentene in the raffinate product. This is demonstrated by the data under the heading of "C$_5$ Product". The C$_5$ product stream is that in which the cyclopentenes are eventually discharged unless earlier removed from the feedstream to the alcohol recovery section of the process. As earlier indicated herein, the presence of large concentrations of cyclopentenes in a feedstream can have a negative impact on downstream processing, and it can be desirable to remove cyclopentenes along with the ether product stream of the inventive process prior to any non-ether compounds being charged to the alcohol recovery section. The data demonstrate that the alternative process is very effective at removing cyclopentenes from the system as shown by the volume percent cyclopentenes in the C$_5$ product being significantly reduced under the alternative process.

Reasonable variations and modifications are possible within the scope of the foregoing disclosure, drawings and appended claims.

That which is claimed is:

1. A process comprising:
passing an etherification reactor effluent as a first feed to first separation means for separating feeds into a first stream comprising a first ether product and a second stream comprising primary alcohols and tertiary olefins;
passing said second stream to a reactor zone containing therein an acidic ion exchange resin and wherein the primary alcohols and tertiary olefins of said second streams react to form a second ether product contained in a reactor effluent stream;
passing a portion of said reactor effluent stream to said first separation means; and
passing the remaining portion of said reactor effluent stream to second separation means for separating said remaining portion of said reactor effluent stream into a third stream comprising a second ether product and a fourth stream comprising hydrocarbons and primary alcohols.

2. A process as recited in claim 1, further comprising: passing said third stream as a third feed to said first separation means.

3. A process as recited in claim 2, further comprising: passing said fourth stream to an alcohol recovery system whereby primary alcohols are recovered from said fourth stream.

4. A process as recited in claim 3, wherein within said alcohol recovery system said fourth stream is contacted with a solvent within a contacting zone to produce a raffinate stream and an extract stream comprising said solvent rich in primary alcohols.

5. A process as recited in claim 4, further comprising: separating said raffinate stream into a fifth stream comprising oxygenates and a sixth stream comprising hydrocarbons.

6. A process as recited in claim 5, further comprising: separating said extract stream into a seventh stream comprising primary alcohols and a eighth stream comprising said solvent lean in primary alcohols.

7. A process as recited in claim 6, further comprising: utilizing said eighth stream as said solvent in said contacting zone.

8. A process as recited in claim 7, wherein said etherification reactor effluent is produced by contacting a hydrocarbon feedstream, comprising hydrocarbons and tertiary olefins, and an alcohol feedstream, comprising primary alcohols, with an acidic ion exchange resin under etherification reaction conditions.

9. A process as recited in claim 8, further comprising: mixing said seventh stream with said alcohol feedstream.

10. A process as recited in claim 1, further comprising:
passing said fourth stream to an alcohol recovery system whereby primary alcohols are recovered from said fourth stream.

11. A process as recited in claim 10, wherein within said alcohol recovery system said fourth stream is contacted with a solvent within a contacting zone to produce a raffinate stream and an extract stream comprising said solvent rich in primary alcohols.

12. A process as recited in claim 11, further comprising:
separating said raffinate stream into a fifth stream comprising oxygenates and a sixth stream comprising hydrocarbons.

13. A process as recited in claim 12, further comprising:
separating said extract stream into a seventh stream comprising primary alcohols and a eighth stream comprising said solvent lean in primary alcohols.

14. A process as recited in claim 13, further comprising:
utilizing said eighth stream as said solvent in said contacting zone.

15. A process as recited in claim 14, wherein said etherification reactor effluent is produced by contacting a hydrocarbon feedstream, comprising hydrocarbons and tertiary olefins, and an alcohol feedstream, comprising primary alcohols, with an acidic ion exchange resin under etherification reaction conditions.

16. A process as recited in claim 15, further comprising:
mixing said seventh stream with said alcohol feedstream.

17. A process comprising:
feeding a first etherification reaction product as a first feed to first separation means for separating feeds into a first stream comprising hydrocarbon, tertiary olefins, and primary alcohols and a second stream comprising a first ether product;
contacting said first stream, under etherification conditions, with an acidic ion exchange resin to produce a second etherification reaction product;
feeding a portion of said second etherification reaction product as a reflux to said first separation means; and
feeding the remaining portion, which is that portion not fed to said first separation means, of said second etherification reaction product to second separation means for separating said remaining portion of said second etherification reaction product into a third stream comprising hydrocarbons and primary alcohols and a fourth stream comprising a second ether product.

18. A process as recited in claim 17, further comprising:
feeding said fourth stream as third feed to said first separation means.

19. A process for producing tert-alkyl ethers comprising:
contacting a mixed stream containing isoamylenes having a double bond on the tertiary carbon atom, methanol, and other non-reactive compounds with acidic ion exchange resin under etherification conditions suitable for reacting at least a portion of the isoamylenes with methanol contained in said mixed streams to produce a first reactor product containing methyl tert-amyl ether, isoamylenes, methanol and other non-reactive compounds;
feeding said first reactor product as a first feed to first separation means for separating feeds into a first stream comprising isoamylenes, methanol and other non-reactive compounds and a second stream comprising methyl tert-amyl ether;
contacting said first stream with acidic ion exchange resin under etherification conditions suitable for reacting a portion of the isoamylenes with methanol contained in said first stream to produce a second reactor product containing methyl tert-amyl ether, methanol and other non-reactive compounds;
feeding a portion of said second reactor product to said first separator means; and
feeding the remaining portion, which is that portion not fed to said first separation means, of said second reactor product to second separation means for separating said remaining portion of said second reactor product into a third stream comprising methanol and other non-reactive compounds and a fourth stream comprising methyl tert-amyl ether.

20. A process for producing tert-alkyl ethers comprising:
contacting a mixed stream containing isobutylenes, methanol, and other non-reactive compounds with acidic ion exchange resin under etherification conditions suitable for reacting at least a portion of the isobutylenes with methanol contained in said mixed streams to produce a first reactor product containing methyl tert-butyl ether, isobutylenes, methanol and other non-reactive compounds;
feeding said first reactor product as a first feed to first separation means for separating feeds into a first stream comprising isobutylenes, methanol and other non-reactive compounds and a second stream comprising methyl tert-butyl ether;
contacting said first stream with acidic ion exchange resin under etherification conditions suitable for reacting a portion of the isobutylenes with methanol contained in said first stream to produce a second reactor product containing methyl tert-butyl ether, methanol and other non-reactive compounds;
feeding a portion of said second reactor product to said first separator means; and
feeding the remaining portion, which is that portion not fed to said first separation means, of said second reactor product to second separation means for separating said remaining portion of said second reactor product into a third stream comprising methanol and other non-reactive compounds and a fourth stream comprising methyl tert-butyl ether.

21. A process comprising:
passing an etherification reactor effluent as a first feed to first separation means for separating feeds into a first stream comprising a first ether product and a second stream comprising primary alcohols and tertiary olefins said first separation means having a rectifying zone and a stripping zone;
passing said second stream to a reactor zone containing therein an acidic ion exchange resin and wherein the primary alcohols and tertiary olefins of said second stream react to form a second ether product contained in a reactor effluent stream;
passing said reactor effluent stream to second separation means for separating said reactor effluent stream into a third stream comprising a second ether product and a fourth stream comprising hydrocarbons and primary alcohols;
cooling said third stream to thereby produce a cooled stream; and
utilizing said cooled stream as a reflux to said first separation means.

22. A process as recited in claim 21, further comprising:
passing said fourth stream to an alcohol recovery system whereby primary alcohols are recovered from said fourth stream.

23. A process as recited in claim 22, wherein within said alcohol recovery system said fourth stream is contacted with a solvent within a contacting zone to produce a raffinate stream and an extract stream comprising said solvent rich in primary alcohols.

24. A process as recited in claim 23, further comprising:
separating said raffinate stream into a fifth stream comprising oxygenates and a sixth stream comprising hydrocarbons.

25. A process as recited in claim 24, further comprising:
separating said extract stream into a seventh stream comprising primary alcohols and an eighth stream comprising said solvent lean in primary alcohols.

26. A process as recited in claim 25, further comprising:

utilizing said eighth stream as said solvent in said contacting zone.

27. A process as recited in claim 26, wherein said etherification reactor effluent is produced by contacting a hydrocarbon feedstream, comprising hydrocarbons and tertiary olefins, and an alcohol feedstream, comprising primary alcohols, with an acidic ion exchange resin under etherification reaction conditions.

28. A process as recited in claim 27, further comprising:
mixing said seventh stream with said alcohol feedstream.

* * * * *